United States Patent [19]

Marchand et al.

[11] Patent Number: 4,758,340
[45] Date of Patent: Jul. 19, 1988

[54] SEALING DEVICE FOR A CHROMATOGRAPHY COLUMN

[75] Inventors: Claude Marchand, Schonenbuch; Michael Schoohf, Allschwil, both of Switzerland

[73] Assignee: Labomatic AG, Allschwil, Switzerland

[21] Appl. No.: 110,228

[22] Filed: Oct. 19, 1987

[30] Foreign Application Priority Data

Oct. 27, 1986 [DE] Fed. Rep. of Germany ....... 3636490

[51] Int. Cl.$^4$ ............................................. B01D 15/08
[52] U.S. Cl. ................... 210/198.2; 210/450; 55/386
[58] Field of Search ...................... 210/198.2, 232, 450, 210/656; 55/386

[56] References Cited

U.S. PATENT DOCUMENTS

| | | | |
|---|---|---|---|
| 3,487,938 | 1/1970 | Patterson | 210/198.2 |
| 3,791,522 | 2/1974 | Eisenbeiss | 210/198.2 |
| 3,904,527 | 9/1975 | Wilhelmson | 210/198.2 |
| 4,093,550 | 6/1978 | Stahl | 210/198.2 |
| 4,131,547 | 12/1978 | Michel | 210/232 |
| 4,187,177 | 2/1980 | Stahl | 210/198.2 |
| 4,283,280 | 8/1981 | Brownlee | 210/198.2 |
| 4,389,313 | 6/1983 | Charney | 210/198.2 |
| 4,451,364 | 5/1984 | Higgins | 210/198.2 |
| 4,551,249 | 11/1985 | Shackelford | 55/386 |
| 4,578,193 | 3/1986 | Shephard | 210/198.2 |
| 4,655,917 | 4/1987 | Shackelford | 210/198.2 |
| 4,670,141 | 6/1987 | Shackelford | 55/386 |

FOREIGN PATENT DOCUMENTS 509591 8/1971 Switzerland ...................... 210/198.2

Primary Examiner—Ernest G. Therkorn

[57] ABSTRACT

The sealing device has a sealing element which can be moved axially relative to the column by means of a positioning ring. A threaded bushing and a threaded ring that is screwed into it enclose the positioning ring. By means of these, the sealing element on the one hand is held at the column and, on the other hand, can be moved by turning the positioning ring. Thus, the connection points of the finished column can be matched to an existing line system.

8 Claims, 1 Drawing Sheet

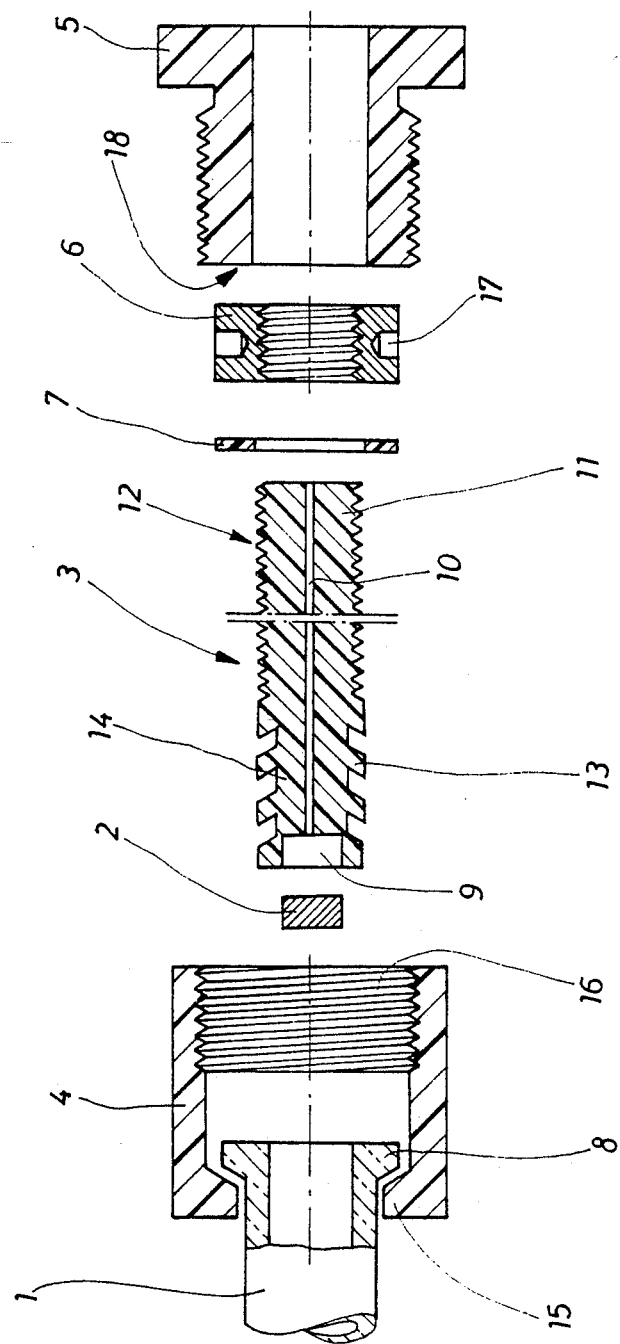

SEALING DEVICE FOR A CHROMATOGRAPHY COLUMN

BACKGROUND OF THE INVENTION

1. Field of the Invention

The present invention relates to a chromatography column and in particular to a new and improved construction of a sealing device containing a sintered body, a sealing element which can be inserted into the column, a threaded bushing having a recess for inserting the column and a section for holding the bushing at the column and a threaded ring which together with said bushing holds the sealing element.

2. Description of the Prior Art

Various designs have become known for sealing chromatography columns.

In the finished column that is described in the DE-OS 21 32 686, this is done by a sealing plug which has a capillary and whose circumference is provided with elastic lips. These lips have a slightly greater outside diameter and are supposed to open towards the outer end of the sealing plug. To prevent the sealing plug from being pressed outwards, one can provide a seal by means of a casting compound.

The disadvantages of this design are that both and matching to the line system are complicated and time consuming.

The CH-PS 509 591 discloses a sealing device where a plug is surrounded by two elastic rubber sealing rings. A spacer bushing is disposed between these. Furthermore, a pressure element is provided which can be moved relative to the plug so as to press the sealing rings against the inside wall of the tube.

The disadvantages of this sealing device are its complicated structure and assembly, as well as its laborious matching into the line system.

The U.S. Pat. No. 4,131,547 describes a finished column for chromatography, where the plug is screwed into the column.

A disadvantage here is the expensive design of the final section of the column.

SUMMARY OF THE INVENTION

Therefore, with the foregoing in mind, it is a primary object of the present invention to provide an improved construction of the sealing device which is not afflicted with the aforementioned drawbacks and limitations of the prior art.

Another object of the present invention relates to a new and improved construction of a sealing device for a chromatography column, which, in its assembled state, offers the capability of moving the sealing element under full system pressure axially relative to the column, in order to equalize the dead space that may have arisen and in order to match the completely assembled column easily to a line system.

The advantages of the invention are essentially the simple structure and simple handling of the sealing device.

BRIEF DESCRIPTION OF THE DRAWING

The invention is described below in terms of the accompanying drawing, which displays an embodiment of the sealing device in an exploded representation.

DESCRIPTION OF THE PREFERRED EMBODIMENT

The sealing device is insertable into and is held at the end of a column 1. The sealing device comprises: a sintered body 2; a sealing element 3; a threaded bushing 4; a threaded ring 5; a positioning ring 6 and a washer 7. A flange 8 is formed at the end section of the column 1. The sealing device is held at this flange 8. The sealing element 3 has a recess 9 to accept the sintered body 3 as well as a through hole 10 in its longitudinal direction. The sealing element 3 has an elongated cylindrical body, e.g. made of plastic, where this body, starting at one end, has a first section 12 that is provided with an outside thread 11, and, adjoining to this, has a second section 14 that is provided with sealing means. The sealing means are formed by sealing lips 13, which are formed at the second section 14 and which open towards the interior end of the sealing element 3.

The threaded bushing 4 is disposed on the end section of the column 1. For this purpose a (not shown) recess has been provided so that the threaded bushing 4 can be placed from the side onto the end section of the column. At one end, the inserted bushing has a section 15 which protrudes inwards, such when the sealing device is mounted, the section 15 contacts the column 1. At its other end, the threaded bushing has an inside thread 16, into which the threaded ring 5 can be screwed.

The positioning ring 6 has an inside thread, as well as holes 17 along its circumference, so that the positioning ring 6 can be moved on the sealing element 3. The sealing ring 6 consists e.g. of metal.

When the sealing device is mounted, the threaded bushing 4 is first placed on the column 1. Then the sealing element 3 with the sintered body 2 and the second section 13 in front is pressed into the column 1. To facilitate this pressing-in process, the positioning ring 6 can first be screwed onto the first section 11. Here one should take care that, in this case, the washer 7 is first placed on the sealing element 3. Then the threaded ring 5 is screwed into the threaded bushing 4. In this way, on the one hand, the section 15 of the threaded bushing 4 contacts the flange 8 of the column 1, and, on the other hand, the positioning ring 6 is disposed in a space that is formed by the front edge 18 of the threaded ring 5 and by the surface of the washer 7 which lies on the column 1. Thus, the position of the sealing element 3 with respect to the column 1 is determined by the positioning ring 6 and can be changed by turning said positioning ring 6. In this way, the connection points of the finished column can be matched to an existing line system.

While there is shown and described a present preferred embodiment of the invention, it is to be distinctly understood that the invention is not limited thereto, but may be otherwise variously embodied and practiced within the scope of the following claims.

We claim:

1. A sealing device for a chromatography column comprising a sintered body, a sealing element inserted into the column and that holds the sintered body, a threaded bushing with an inside thread, which has a recess into which the column has been inserted as well as a section brought into contact with the column in order to hold the threaded bushing at the column, and a threaded ring which is screwed into the threaded bushing and which, together with said bushing, holds the sealing element at the column, wherein said sealing element has a first section, which is provided with an outside thread and, adjoining this, has a second section that is provided with sealing means, where said second section has been inserted into the column, and wherein further, a positioning ring is screwed onto the sealing element and is disposed between the threaded bushing and the threaded ring in such a fashion that the positioning ring is held rotatably at the end of the column, so as to move the sealing element in the axial direction with respect to the column.

2. A device of claim 1, wherein said sealing means is at least one sealing lip, which is formed at the second section.

3. A device of claim 2, wherein a number of sealing lips is provided, which are formed so as to lie next to one another.

4. A device of claim 2 or 3, wherein said sealing lip is formed so as to slant with respect to the axis of the sealing element.

5. A device of claim 4, wherein said sealing lip is designed at a slant with respect to the direction of the end of the sealing element that is intended for insertion.

6. A device of claim 1, wherein a washer is situated between the end of the column and the positioning ring.

7. A device of claim 1, wherein said threaded bushing and the threaded ring consist of plastic.

8. A device of claim 1, wherein said positioning ring consist of plastic.

* * * * *

UNITED STATES PATENT AND TRADEMARK OFFICE
CERTIFICATE OF CORRECTION

PATENT NO. : 4,758,340
DATED : July 19, 1988
INVENTOR(S) : Marchand et al.

It is certified that error appears in the above-identified patent and that said Letters Patent are hereby corrected as shown below:

Col. 1, line 27 after "both" insert -- replacement --

Signed and Sealed this

Twenty-fourth Day of January, 1989

Attest:

DONALD J. QUIGG

Attesting Officer

Commissioner of Patents and Trademarks